US012285454B2

United States Patent
Chen et al.

(10) Patent No.: US 12,285,454 B2
(45) Date of Patent: Apr. 29, 2025

(54) ANTI-AGING CHINESE HERB EXTRACT, EXTRACTION METHOD AND USE THEREOF

(71) Applicant: HEALTH LIFE BIOSCIENCES INC, Arcadia, CA (US)

(72) Inventors: Jin Chen, Sichuan (CN); Yunyan He, Sichuan (CN); Jun Su, Sichuan (CN); Ai Li, Sichuan (CN)

(73) Assignee: HEALTH LIFE BIOSCIENCES INC, Arcadia, CA (US)

( * ) Notice: Subject to any disclaimer, the term of this patent is extended or adjusted under 35 U.S.C. 154(b) by 478 days.

(21) Appl. No.: 17/772,728

(22) PCT Filed: Aug. 10, 2020

(86) PCT No.: PCT/CN2020/108196
§ 371 (c)(1),
(2) Date: Apr. 28, 2022

(87) PCT Pub. No.: WO2021/088446
PCT Pub. Date: May 14, 2021

(65) Prior Publication Data
US 2022/0347250 A1    Nov. 3, 2022

(30) Foreign Application Priority Data
Nov. 6, 2019   (CN) .......................... 201911077838.X (51) Int. Cl.
  *A61K 36/258*   (2006.01)
  *A61K 36/481*   (2006.01)
  *G01N 30/02*   (2006.01)
  *G01N 30/36*   (2006.01)
  *G01N 30/86*   (2006.01)

(52) U.S. Cl.
  CPC .......... *A61K 36/258* (2013.01); *A61K 36/481* (2013.01); *G01N 30/36* (2013.01); *G01N 30/8686* (2013.01); *A61K 2236/53* (2013.01); *A61K 2236/55* (2013.01); *G01N 2030/027* (2013.01)

(58) Field of Classification Search
  CPC ................................................... A61K 36/258
  See application file for complete search history.

(56) References Cited

U.S. PATENT DOCUMENTS

| 2015/0099032 A1* | 4/2015 | Roumayeh | A23L 33/40 426/2 |
| 2017/0128514 A1* | 5/2017 | Du | A61P 7/02 |
| 2021/0038668 A1* | 2/2021 | Han | A61K 36/537 |

FOREIGN PATENT DOCUMENTS

| CN | 1709462 A | 12/2005 | |
| CN | 101269113 A | 9/2008 | |
| CN | 101439078 A | 5/2009 | |
| CN | 101966223 A | 2/2011 | |
| CN | 104173700 A | 12/2014 | |
| CN | 106727807 A | 5/2017 | |
| CN | 107383144 A | 11/2017 | |
| CN | 111686148 A | 9/2020 | |
| WO | WO-2018027081 A1 * | 2/2018 | A23G 3/34 |

OTHER PUBLICATIONS

Park et al., Korean red ginseng extract induces apoptosis and decreases telomerase activity in human leukemia cells, J Ethnopharm, (121: 304-312 (2009). (Year: 2009).*
Chun-Yan Shen et al. "Anti-ageing active ingredients from herbs and nutraceuticals used in traditional Chinese medicine; pharmacological mechanisms and implications for drug discovery" British Journal of Pharmacology, vol. vol. 174, No. 11., Dec. 31, 2017 (Dec. 31, 2017), pp. 1395-1425, abstract, table 1, figure 1, p. 1400 left-hand column last paragraph-right-hand column paragraph 1.
International search report of PCT/CN/2020/108196.

* cited by examiner

*Primary Examiner* — Gina C Justice (57) ABSTRACT

The present invention discloses an anti-aging Chinese herb extract, an extraction method and a use thereof. The *ginseng-Astragalus membranaceus* extract of the present invention comprises 20 to 30% of astragaloside, 1 to 5% of ginsenoside Rg1, 2 to 6% of ginsenoside Re, 0.2 to 0.5% of ginsenoside Rb1. There are 17 characteristic peaks in high-performance liquid chromatography fingerprints of the extract. The extract can effectively improve activity of telomerase, delay cell aging, and can be applied to preparation of an anti-aging product.

14 Claims, 1 Drawing Sheet

# ANTI-AGING CHINESE HERB EXTRACT, EXTRACTION METHOD AND USE THEREOF

CROSS REFERENCE TO RELATED APPLICATION

This application is International Patent Application No. PCT/CN2020/108196, filed on Aug. 10, 2020, which claims priority benefit of Chinese Patent Application No. 201911077838.X, filed on Nov. 6, 2019, and the entire contents of which are incorporated herein by reference.

TECHNICAL FIELD

The present invention relates to a technical field of a Chinese herb extract and an extraction method, in particular, to an anti-aging Chinese herb extract, an extraction method and a use thereof.

BACKGROUND

A cell is a basic unit of organism structure and function, and also a basic unit of biological aging. Cell aging refers to gradual deterioration of cell proliferation, differentiation and physiological functions over time during performing life activities. The life course of a cell goes through several stages of undifferentiation, differentiation, growth, maturity, senescence and death.

Although aging and death are inevitable, it is possible to delay aging, especially by trying to avoid pathological aging. It is reported that by 2050, the aged people over 60 years old will reach 2 billion, and account for about 20~30% of the total population. In the face of accelerating process of aging of population and general trend of increasing life expectancy, it has become a major concern of social science and life science to ensure the elder to enjoy good health and high quality of life. In-depth research on more effective anti-aging products will be beneficial to realization of "healthy aging" in China. Therefore, it is of great scientific significance and social value to carry out anti-aging research and develop anti-aging products.

SUMMARY

For a long time, people have been exploring ways to delay aging and prolong life. The research on prolonging life in traditional Chinese medicine has a long history, precious documentary records and rich practical experience. It has also been recorded that many Chinese medicinal materials have anti-aging effects. In research and development of anti-aging products, researchers found that although many Chinese medicinal materials have anti-aging effects, their anti-aging effects are not very ideal or significant. Even if extracts with higher content of active substances are used, the anti-aging activities of Chinese medicinal materials are still difficult to be further improved.

Therefore, it has been an urgent problem to be solved in this field to further improve the anti-aging activities of Chinese medicinal materials and obtain extracts that can delay aging more effectively.

The purpose of the present invention is to provide an anti-aging Chinese herb extract and its extraction method, so as to obtain a product with better anti-aging effect.

To solve the above problems, the present invention provides a composition comprising the following components in part by weight: 20 to 30 parts of astragaloside, 1 to 5 parts of ginsenoside Rg1, 2 to 6 parts of ginsenoside Re, and 0.2 to 0.5 parts of ginsenoside Rb1.

Further, the composition comprises the following components in part by weight: 22 to 28 parts of astragaloside, 1.8 to 4 parts of ginsenoside Rg1, 3 to 5 parts of ginsenoside Re, and 0.2 to 0.3 parts of ginsenoside Rb1.

The present invention also provides an extract, of which raw materials comprising, in part by weight, 1 part of *ginseng* and/or American *ginseng*, and 4 to 8 parts of *Astragalus membranaceus*, preferably 4 to 6 parts of *Astragalus membranaceus*, wherein the extract comprises 20 to 30% of astragaloside, 1 to 5% of ginsenoside Rg1, 2 to 6% of ginsenoside Re, and 0.1 to 0.5% of ginsenoside Rb1.

Further, the extract comprises 22 to 28% of astragaloside, 1.8 to 4% of ginsenoside Rg1, 3 to 5% of ginsenoside Re, and 0.2 to 0.3% of ginsenoside Rb1.

Further, a content of total saponins in the extract is from 75 to 95% and a content of total polysaccharide is from 3 to 10%.

Furthermore, the content of total saponins is 80~90%, and the content of total polysaccharides is 5~8%.

Further, the *ginseng* is *ginseng* and/or a *ginseng* processed product.

Further, the *ginseng* processed product is selected from one or several of a raw sun-dried *ginseng*, a red *ginseng* and an active *ginseng*.

The present invention also provides an extract comprising ginsenoside Re, wherein there are at least 6 characteristic peaks in high-performance liquid chromatography fingerprints of the extract, and wherein taking the characteristic peak of ginsenoside Re as a reference peak, relative retention times for the 6 characteristic peaks with respect to the reference peak are 0.95, 1.00, 1.80, 2.13, 2.36, and 3.20 respectively.

Further, the fingerprints further comprise 11 characteristic peaks, wherein relative retention times for the 11 characteristic peaks with respect to the reference peak are 1.66, 1.69, 1.73, 1.86, 1.88, 1.94, 1.99, 2.02, 2.28, 2.40, and 2.45 respectively.

Further, the raw materials comprise in part by weight, 1 part of *ginseng* and/or American *ginseng*, and 4 to 8 parts of *Astragalus membranaceus*, preferably 4 to 6 parts of *Astragalus membranaceus*.

Further, the *ginseng* is *ginseng* and/or a *ginseng* processed product.

Further, the *ginseng* processed product is selected from one or several of a raw sun-dried *ginseng*, a red *ginseng* and an active *ginseng*.

Further, relative peak areas of characteristic peaks with relative retention times of 0.95, 1.00, 1.80, 2.13, 2.36 and 3.20 were 48.41%, 100.00%, 107.04%, 48.70%, 340.51% and 54.83%, respectively.

Further, relative peak areas of characteristic peaks with relative retention times of 1.66, 1.69, 1.73, 1.86, 1.88, 1.94, 1.99, 2.02, 2.28, 2.40 and 2.45 are 9.52%, 17.21%, 2.61%, 4.16%, 22.88%, 10.92%, 16.34%, 8.33%, 3.37%, 5.14% and 14.59%, respectively.

The relative retention time and the relative peak area mentioned above can fluctuate within a reasonable range. If it fluctuates within 5% of its value, it shall be deemed to fall into the scope of protection required by the present invention.

The present invention also provides a detection method of high-performance liquid chromatography (HPLC) fingerprints, which is used for a qualitative and/or quantitative detection by HPLC, wherein HPLC conditions comprise:

column: C18 silica gel column;
mobile phase: water and acetonitrile, and
a gradient elution procedure:

| Time (min) | Water (V %) | Acetonitrile (V %) |
|---|---|---|
| 0 | 80~90 | 10~20 |
| 30~35 | 60~70 | 30~40 |
| 70~85 | 10~30 | 70~90 |

Further, the elution procedure is used:

| Time (min) | Water (V %) | Acetonitrile (V %) |
|---|---|---|
| 0 | 85 | 16 |
| 33 | 66 | 34 |
| 78.5 | 20 | 80 |

Further, the detection method comprises conditions as follows:
① column size: 150*3.9 mm, 5 μm;
② column temperature: 25~35° C.; preferably 30° C.;
③ flow rate: 0.8~1.2 mL/min; preferably 1.00 mL/min;
④ detection wavelength: 200~205 nm, preferably 203 nm.

The present invention also provides a preparation method of natural plant extract, comprises: (1) performing extraction from the raw materials with water; (2) performing enrichment with macroporous adsorption resin; (3) performing enzymolysis; (4) performing membrane filtration wherein molecular weight cut-of is 200~1000 Da; and (5) performing solid-liquid separation.

The plant is selected from one or two of ginseng, American ginseng, and/or Astragalus membranaceus. That is, the plant can be one of ginseng, American ginseng, and Astragalus membranaceus. It can also be a mixed extract of two: ① ginseng and Astragalus membranaceus, ② American ginseng and Astragalus membranaceus, ③ ginseng and American ginseng, or a mixed extract of three: ginseng, American ginseng, and Astragalus membranaceus.

Further, the ginseng is ginseng and/or a ginseng processed product.

Further, the ginseng processed product is selected from one or several of a raw sun-dried ginseng, a red ginseng and an active ginseng.

The raw sun-dried ginseng is a commercial ginseng, also known as white ginseng, which is a product obtained by washing and drying after the ginseng root is picked.

The red ginseng is dried root and rhizome after steaming cultivated ginseng of the araliaceae family wherein the cultivated ginseng is picked in autumn, washed and steamed, and dried. Common red ginseng is used in the present invention.

The active ginseng is a freeze-dried ginseng at low temperature. The product is called as an "active ginseng", because it can absorb water quickly when put it in water and its appearance can be restored to a state similar to a fresh ginseng.

The raw sun-dried ginseng, the red ginseng, and the active ginseng are common in the field of processed products of ginseng, can be commercially available, or can be prepared through the existing technology. The obtained raw sun-dried ginseng, red ginseng, and active ginseng can be applied to the present invention. A raw sun-dried ginseng, a red ginseng, and an active ginseng which meet national standards (national standard file: GB/T 22536-2018 of raw sun-dried ginseng grading quality; GB/T 22538-2018 of red ginseng grading quality; GB/T 22535-2018 of active ginseng grading quality) are preferred.

In an embodiment of the present invention, in the step of extraction with water, a liquid/material ratio of water to the raw material is 5-15:1 mL/g.

Further, the extraction with water is repeated 1 to 4 times, more preferably 2 times.

In an embodiment of the present invention, the enrichment with macroporous adsorption resin is to obtain a part by passing an extraction liquid extracted with water through the macroporous adsorption resin to performing adsorption, washing with water, 10~40% ethanol, and 60~80% ethanol successively, and collecting a 60~80% ethanol eluent.

Further, washing was performed with water, 25-30% ethanol, and 70~80% ethanol successively, and a 70~80% ethanol eluent is collected.

Furthermore, the macroporous adsorption resin is non-polar or weak polar macroporous adsorption resin. Preferably, the macroporous adsorption resin is selected from D-101, HPD-10, X-5, and AB-8.

In an embodiment of the present invention, the enzymolysis is enzymolysis of the material obtained after the enrichment with macroporous adsorption resin.

One or more of glycosidase, pectinase, amylase can be used in the enzymolysis.

Further, one or more of β-glucosidase, Xylanase, lactase, arabinofuranosidase, pectin lyase, and amylase can be used in the enzymolysis.

In an embodiment of the present invention, the enzyme is a complex enzyme composed of β-glucosidase and Xylanase at a weight ratio of 2-4:1.

Further, the enzymolysis conditions are performing enzymolysis with the complex enzyme of 0.2 to 1.0% by a weight of the raw material at pH of 5 to 6 at 40 to 55° C.

Further, the amount of the complex enzyme is 0.4 to 0.6%.

Further, the enzymolysis time is 3 to 8 h. Furthermore, the enzymolysis time is 4 to 6 h.

The present invention also provides one of the following extracts prepared by the above method: (1) a ginseng extract; (2) a American ginseng extract; (3) an Astragalus membranaceus extract; (4) a mixed extract of ginseng and American ginseng; (5) a mixed extract of ginseng and Astragalus membranaceus; (6) a mixed extract of American ginseng and Astragalus membranaceus; (7) a mixed extract of ginseng, American ginseng and Astragalus membranaceus.

The present invention also provides a composition comprising the following raw materials in part by weight: 1 part of the ginseng extract and/or the American ginseng extract, and 5 to 14 parts of the Astragalus membranaceus extract. Further, the composition comprises 1 part of the ginseng extract and/or the American ginseng extract and 5.5~11 parts of the Astragalus membranaceus extract.

The present invention also provides a use of one or more of the extracts, the extraction methods and the compositions in preparing products that can improve the telomerase activity and/or improve the telomere length. The extracts described herein may be selected from all of the extracts mentioned above, and not limited to the extracts defined by the compositions or fingerprints.

Further, the product is a telomerase activator.
Further, the product is an anti-aging product.
Furthermore, the product is a product for delaying cell aging.

The invention also provides a product comprising one or more of the extracts and compositions. The extracts described herein may be selected from all of the extracts, and not limited to the extracts defined by the compositions or fingerprints.

The products in the present invention comprise but are not limited to food, medicine and health care products.

In addition to the above-mentioned extracts or compositions, the above-mentioned products may also comprise an excipient and an auxiliary ingredient.

The pharmaceutical acceptable excipient mentioned in the present invention refers to all additional materials except for a main drug in a medicine. The excipient shall have the following properties: (1) no toxic effect on human body and few side effect; (2) stable chemical properties which are not easily affected by a temperature, pH, storage time, etc.; (3) no incompatibility with the main drug, not affecting efficacy and quality inspection of the main drug; (4) no interaction with packaging materials. The excipient of the present invention comprises, but are not limited to a filler (a diluent), a lubricant (a flow aid or an anti-adhesion agent), a dispersant, a wetting agent, an adhesive, a regulator, a solubilizer, an antioxidant, an antibacterial agent, an emulsifier, a disintegrating agent and so on. The adhesive comprises syrup, gum Arabic, gelatin, sorbitol, *Astragalus* gum, cellulose and its derivatives (such as microcrystalline cellulose, sodium carboxymethyl cellulose, ethyl cellulose or hydroxypropyl methyl cellulose, etc.), gelatin pulp, syrup, starch paste or polyvinyl pyrrolidone, etc. The fillers comprise lactose, sugar powder, dextrin, starch and its derivatives, cellulose and its derivatives, inorganic calcium salts (such as calcium sulfate, calcium phosphate, calcium hydrogen phosphate, precipitated calcium carbonate, etc.), sorbitol or glycine and so on. The lubricant comprises aerosil, magnesium stearate, talcum powder, aluminum hydroxide, boric acid, hydrogenated vegetable oil, polyethylene glycol and so on. The disintegrating agent comprises starch and its derivatives (such as sodium carboxymethyl starch, sodium starch glycolate, pre-gelatinized starch, modified starch, hydroxypropyl starch, corn starch, etc.), polyvinyl pyrrolidone or microcrystalline cellulose and so on. The wetting agent comprises sodium dodecyl sulfate, water or alcohol and so on. The antioxidant comprises sodium sulfite, sodium bisulfite, sodium metabisulfite, dibutyl benzoic acid, and so on. The antibacterial agent comprises 0.5% phenol, 0.3% cresol, 0.5% trichlorot-butyl alcohol and so on. The regulator comprises hydrochloric acid, citrate, potassium hydroxide (sodium), sodium citrate and buffer (including sodium dihydrogen phosphate and disodium hydrogen phosphate). The emulsifier comprises polysorbates-80, sorbitan oleate, pluronic F-68, lecithin, fabaceous lecithin and so on. The solvent comprises Tween-80, bile, glycerin and so on.

The auxiliary ingredient may be Chinese medicinal materials or their extracts, chemicals and other substances having the same effect or function as the extract or composition of the present invention, or active substances having other functions or effects.

The beneficial effects of the present invention are as follows.

The *ginseng* extract, the *Astragalus membranaceus* extract and the mixed extract extracted from the *ginseng* and the *Astragalus membranaceus* by the extraction method of the present invention can effectively improve activity of telomerase and have high anti-aging activity, and can be used to prepare anti-aging products.

The anti-aging activity of the *ginseng-Astragalus membranaceus* extract of the invention is superior to that of any extract at the same concentration, indicating that the combination of the *ginseng* extract and the *Astragalus membranaceus* extract of the invention plays a synergistic effect and significantly improves its anti-aging performance.

DETAILED DESCRIPTION

Figure 1:
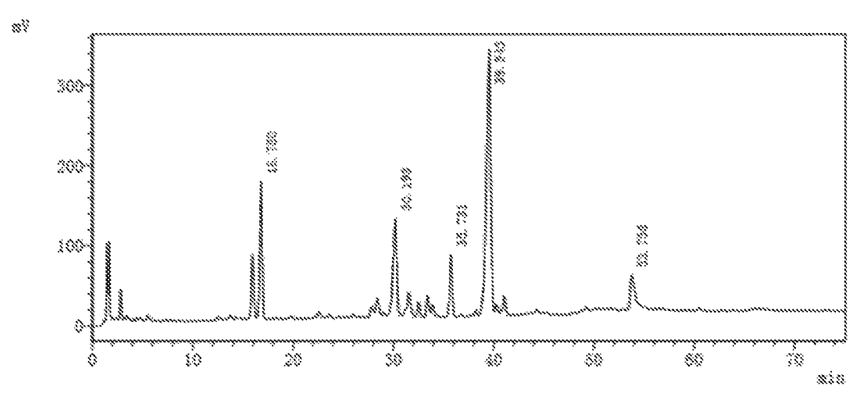
FIG. 1 illustrates the fingerprints of *ginseng-Astragalus membranaceus* extract of Example 1 of the present invention.

The invention is further explained by specific embodiments and specific tests.

Example 1

10 g of medicinal powders (1.67 g of *ginseng*, 8.33 g of *Astragalus membranaceus*) were weighed, and added with 100 mL of water to soak for 3 hours, then heated to perform reflux extraction for 2 hours, and filtered. The filter residue was then reflux-extracted with 80 mL of water for 2 hours, and filtered, and the filtrate was pooled. The pooled filtrate was passed through macroporous adsorption resin D101 and then washed with water, 20% ethanol, and 70% ethanol respectively. The 70% ethanol eluant was collected, added with 0.5% (by mass of the medicinal powder) of the complex enzyme (β-glucosidase and xylanase at the weight ratio of 2:1) after removing the ethanol, adjusted to pH of 5 to 6, stirred at 40 to 55° C. for 4 hours, and filtered. The filtrate was membrane-filtered with a ceramic nanofiltration membrane (molecular weight cut-off of 200-1000 Da), concentrated, and spray-dried to obtain 11.0 mg of the *ginseng-Astragalus membranaceus* extract of the present invention (the yield of 0.110%).

TABLE 1

| Analysis Item | Ginseng-Astragalus Membranaceus Extract | | | | | | |
|---|---|---|---|---|---|---|---|
| Column | C18 column (150 * 3.9 mm), column temperature of 37° C. | | | | | | |
| Detector | 203 nm | | | | | | |

| | | Time (min) | | | | | Total flow rate |
|---|---|---|---|---|---|---|---|
| | | 0 | 33 | 78.5 | 82 | 82.5 | 90 |
| Mobile Phase | Water (%) | 85 | 66 | 20 | 20 | 85 | 85 | 1.00 mL/min |
| | Acetonitrile (%) | 15 | 34 | 80 | 80 | 15 | 15 | |

TABLE 1-continued

| | |
|---|---|
| Solvent | Methanol |
| References | Astragaloside, ginsenoside Rg1, ginsenoside Re, ginsenoside Rb Injection Volume of 10 μL |
| Sample | Millipore Filter, Injection Volume of 10 μL. |

TABLE 2

| Peak Number | Retention Time | Relative Retention Time | Peak Area | Relative Peak Area | Area % | Content % |
|---|---|---|---|---|---|---|
| 1 (ginsenoside Rg1) | 15.943 | 0.95 | 1365658 | 48.41% | 5.943% | 2.806% |
| 2 (ginsenoside Re) | 16.780 | 1.00 | 2821205 | 100.00% | 12.277% | 4.213% |
| 3 | 27.838 | 1.66 | 268658 | 9.52% | 1.169% | |
| 4 | 28.399 | 1.69 | 485506 | 17.21% | 2.113% | |
| 5 | 29.050 | 1.73 | 73623 | 2.61% | 0.320% | |
| 6 (astragaloside) | 30.193 | 1.80 | 3019883 | 107.04% | 13.141% | 25.322% |
| 7 (ginsenoside Rb1) | 31.203 | 1.86 | 117290 | 4.16% | 0.510% | 0.232% |
| 8 | 31.548 | 1.88 | 645376 | 22.88% | 2.808% | |
| 9 | 32.524 | 1.94 | 308034 | 10.92% | 1.340% | |
| 10 | 33.406 | 1.99 | 461005 | 16.34% | 2.006% | |
| 11 | 33.915 | 2.02 | 235129 | 8.33% | 1.023% | |
| 12 | 35.731 | 2.13 | 1373974 | 48.70% | 5.979% | |
| 13 | 38.200 | 2.28 | 94937 | 3.37% | 0.413% | |
| 14 | 39.545 | 2.36 | 9606382 | 340.51% | 41.803% | |
| 15 | 40.254 | 2.40 | 145125 | 5.14% | 0.632% | |
| 16 | 41.063 | 2.45 | 411738 | 14.59% | 1.792% | |
| 17 | 53.758 | 3.20 | 1546825 | 54.83% | 6.731% | |

Example 2

10 g of the *ginseng* powder was weighed, and added with 100 mL of water to soak for 3 hours, then heated to perform reflux extraction for 2 hours, and filtered. The filter residue was then reflux-extracted with 80 mL of water for 2 hours, and filtered, and the filtrate was pooled. The pooled filtrate was passed through macroporous adsorption resin D101 and then washed with water, 20% ethanol, and 70% ethanol respectively. The 70% ethanol eluant was collected, added with 0.5% (by mass of the medicinal powder) of the complex enzyme (β-glucosidase and xylanase at the weight ratio of 2:1) after removing the ethanol, adjusted to pH of 5 to 6, stirred at 40 to 55° C. for 4 hours, and filtered. The filtrate was membrane-filtered with a ceramic nanofiltration membrane (molecular weight cut-off of 200-1000 Da), concentrated, and spray-dried to obtain 7.5 mg of the *ginseng* extract (the yield of 0.075%).

Example 3

10 g of the *Astragalus membranaceus* powder was weighed, and added with 100 mL of water to soak for 3 hours, then heated to perform reflux extraction for 2 hours, and filtered. The filter residue was then reflux-extracted with 80 mL of water for 2 hours, and filtered, and the filtrate was pooled. The pooled filtrate was passed through macroporous adsorption resin D101 and then washed with water, 20% ethanol, and 70% ethanol respectively. The 70% ethanol eluant was collected, added with 0.5% (by mass of the medicinal powder) of the complex enzyme (β-glucosidase and xylanase at the weight ratio of 2:1) after removing the ethanol, adjusted to pH of 5 to 6, stirred at 40 to 55° C. for 4 hours, and filtered. The filtrate was membrane-filtered with a ceramic nanofiltration membrane (molecular weight cut-off of 200-1000 Da), concentrated, and spray-dried to obtain 11.8 mg of the *Astragalus membranaceus* extract (the yield of 0.118%).

In practice, the yield of the extract in the above examples can fluctuate within a reasonable range, such as 5% above or below its value.

Example 4

10 g of medicinal powders (1.67 g of *ginseng*, 8.33 g of *Astragalus membranaceus*) were weighed, and added with 100 mL of water to soak for 3 hours, then heated to perform reflux extraction for 1.5 hours, and filtered. The filter residue was then reflux-extracted with 100 mL of water for 1.5 hours, and filtered, and the filtrate was pooled. The pooled filtrate was passed through macroporous adsorption resin D101 and then washed with water, 30% ethanol, and 80% ethanol respectively. The 80% ethanol eluant was collected, added with 0.4% (by mass of the medicinal powder) of the complex enzyme (β-glucosidase and xylanase at the weight ratio of 4:1) after removing the ethanol, adjusted to pH of 5 to 6, stirred at 40 to 55° C. for 6 hours, and filtered. The filtrate was membrane-filtered with a ceramic nanofiltration membrane (molecular weight cut-off of 200-1000 Da), concentrated, and spray-dried to obtain the *ginseng-Astragalus membranaceus* extract of the present invention. By HPLC analysis, the *ginseng-Astragalus membranaceus* extract prepared in this Example contained 23.456% of astragaloside, 1.985% of ginsenoside Rg1, 3.669% of ginsenoside Re and 0.209% of ginsenoside Rb1.

Example 5

10 g of medicinal powders (1.67 g of *ginseng*, 8.33 g of *Astragalus membranaceus*) were weighed, and added with 100 mL of water to soak for 4 hours, then heated to perform reflux extraction for 1.5 hours, and filtered. The filter residue was then reflux-extracted with 100 mL of water for 1.5 hours, and filtered, and the filtrate was pooled. The pooled filtrate was passed through macroporous adsorption resin D101 and then washed with water, 25% ethanol, and 70% ethanol respectively. The 70% ethanol eluant was collected, added with 0.5% (by mass of the medicinal powder) of the complex enzyme (β-glucosidase and xylanase at the weight ratio of 3:1) after removing the ethanol, adjusted to pH of 5 to 6, stirred at 40 to 55° C. for 5 hours, and filtered. The filtrate was membrane-filtered with a ceramic nanofiltration membrane (molecular weight cut-off of 200-1000 Da), concentrated, and spray-dried to obtain the *ginseng-Astragalus membranaceus* extract of the present invention. By HPLC analysis, the *ginseng-Astragalus membranaceus* extract prepared in this Example contained 22.498% of astragaloside, 1.906% of ginsenoside Rg1, 3.235% of ginsenoside Re and 0.217% of ginsenoside Rb1.

Example 6

10 g of medicinal powders (1.67 g of *ginseng*, 8.33 g of *Astragalus membranaceus*) were weighed, and added with 100 mL of water to soak for 3 hours, then heated to perform reflux extraction for 2 hours, and filtered. The filter residue was then reflux-extracted with 100 mL of water for 2 hours, and filtered, and the filtrate was pooled. The pooled filtrate was passed through macroporous adsorption resin D101 and then washed with water, 25% ethanol, and 80% ethanol respectively. The 80% ethanol eluant was collected, added with 0.6% (by mass of the medicinal powder) of the complex enzyme (β-glucosidase and xylanase at the weight ratio of 4:1) after removing the ethanol, adjusted to pH of 5 to 6, stirred at 40 to 55° C. for 5 hours, and filtered. The filtrate was membrane-filtered with a ceramic nanofiltration membrane (molecular weight cut-off of 200-1000 Da), concentrated, and spray-dried to obtain the *ginseng-Astragalus membranaceus* extract of the present invention. By HPLC analysis, the *ginseng-Astragalus membranaceus* extract prepared in this Example contained 22.956% of astragaloside, 2.085% of ginsenoside Rg1, 3.726% of ginsenoside Re and 0.213% of ginsenoside Rb1.

Example 7

Different batches of *ginseng* and *Astragalus membranaceus* were extracted according to the ratio and the method described in Example 1. The contents of astragaloside, ginsenoside Rg1, ginsenoside Re and ginsenoside Rb1 in the extract were detected, and the contents of total saponins and total polysaccharides were determined at the same time. The results were shown in Table 2. The contents of total saponins and polysaccharides were determined by conventional methods.

Example 8

A composition, was obtained by mixing 2 mg *ginseng* extract prepared in Example 2 and 14.2 mg *Astragalus membranaceus* extract prepared in Example 3.

Example 9

A composition, was obtained by mixing 2 mg *ginseng* extract prepared in Example 2 and 17.0 mg *Astragalus membranaceus* extract prepared in Example 3.

The beneficial effects of the extract of the present invention are illustrated by the following tests:

Test Example 1

1. Main Reagents
   Telomerase Activity Assay Kit (Roche, Switzerland);
   CCL137 human fibroblast cell lines (American Type Culture Collection (ATCC));
   Ginseng-Astragalus membranaceus extract: the extract prepared in Example 1 of the present invention;
   Astragalus membranaceus extract: the *Astragalus membranaceus* extract prepared in Example 3 of the present invention;
   Ginseng extract: the *ginseng* extract prepared in Example 2 of the present invention.
Method
The effects of different extracts on the telomerase activity were detected by PCR-ELISA. Principle: This method is based on establishment of Telomeric Repeat Amplification Protocol (TRAP), which is used for PCR Amplification of telomerase mediated derivatives and combined with the subsequent ELISA method.
Experimental Procedure:
(1) Preparation of Cell Extracts
   A cell suspension was prepared by conventional methods, and then centrifuged for 10 min at 3000 g at 2 to 8° C. to form a cell precipitate. The supernatant was carefully removed and the cell precipitate was re-suspended with PBS and centrifuged repeatedly at 3000 g for 10 min. The supernatant was carefully sucked out, the cell precipitate was added with 200 μl of lysis reagent and was re-suspended, and pre-cooled on ice and stirred for at least 3 times, and incubated in ice for 30 min, centrifuged at 16000 g at 2-8° C. for 20 min, and then transferred to a new EP tube.
(2) Amplification Steps of Telomerase Repeat Sequence (TRAP Reaction)
   All operation steps are performed on ice. The ice box was prepared in advance. For the samples of each group, to the PCR amplification tube, the 25 μl of reaction mixture is added, 2 μl of cell extract was added and a sterile double steaming water was supplemented to the total volume of 50 μl Amplification and extension of primers were performed in

TABLE 2

| Batch Number | Astragaloside (%) | Ginsenoside Rg1 (%) | Ginsenoside Re (%) | Ginsenoside Rb1 (%) | Total Saponins (%) | Total Polysaccharides (%) |
| --- | --- | --- | --- | --- | --- | --- |
| 20180412 | 23.468 | 2.512 | 3.986 | 0.245 | 85.62 | 6.32 |
| 20180624 | 27.623 | 2.963 | 4.356 | 0.238 | 89.54 | 5.89 |
| 20180711 | 24.369 | 2.778 | 4.012 | 0.269 | 84.83 | 5.98 |
| 20181008 | 23.478 | 2.402 | 4.214 | 0.208 | 88.64 | 5.33 |
| 20190114 | 26.521 | 2.268 | 3.926 | 0.297 | 84.65 | 6.07 |
| 20190325 | 22.589 | 3.012 | 4.386 | 0.301 | 82.34 | 7.38 |
| 20190409 | 25.354 | 2.598 | 3.826 | 0.246 | 87.66 | 5.62 | a PCR instrument. PCR reaction conditions: 94° C. of inactivation for 5 min, 94° C. for 30 s, 55° C. for 30 s, a total of 33 cycles, 72° C. for 10 min, and termination reaction.

(3) ELISA Assay

For the sample of each group, to the EP tube, 20 μl of the denaturing reagent were added and marked, and 5 μl of the obtained product after the PCR amplification was added. The EP tubes were incubated at 20° C. for 10 min, and each of the EP tubes was added and mixed with 225 μl of the hybridization buffer. 100 μl of mixture from each of the groups was added to the microplate and incubated in the oscillator at 37° C. at 300 rpm for two hours. After the hybridization buffer was poured out, each well was washed three times and added with 100 μl of anti-DIG-POD working solution, covered with a lid, and incubated for 30 min on a shaker at 300 rpm at 20° C. After the supernatant was removed, each well was washed with 250 μl of the washing solution 5 times, 1 min each time. Each well was added with 100 μl of TMB fifth solution and preheat to the room temperature, and then incubated on the shaker at 300 rpm for 12 min and then added with 100 μl of the termination reagent to terminate the reaction. The absorbance value is then detected at 450 nm using the microplate reader and and A690 nm was taken as a reference, and the value of the negative control will be subtracted from the absorption value for the sample of each group. If the difference in absorption values (AA) is higher than 0.2 (A450 nm-A690 nm), it can be considered as telomerase positive.

The test results were analyzed and processed by a SPSS18.0 statistical software. Analysis of variance was used for statistics. The data in each group were pairwise compared using the SNK method. When P<0.05, the difference was considered to be statistically significant.

Samples to be Tested (all of which are Aqueous Solution):

Low Concentration Group:

A1: the solution of the *ginseng-Astragalus membranaceus* extract, at concentration of 25 μg/ml;

B1: the solution of the *Astragalus membranaceus* extract, at concentration of 25 μg/ml;

C1: the solution of the *ginseng* extract, at concentration of 25 μg/ml;

Medium Concentration Group:

A2: the solution of the *ginseng-Astragalus membranaceus* extract, at concentration of 50 μg/ml;

B2: the solution of the *Astragalus membranaceus* extract, at concentration of 50 μg/ml;

C2: the solution of the *ginseng* extract, at concentration of 50 μg/ml;

High Concentration Group:

A3: the solution of the *ginseng-Astragalus membranaceus* extract, at concentration of 100 μg/ml;

B3: the solution of the *Astragalus membranaceus* extract, at concentration of 100 μg/ml;

C3: the solution of the *ginseng* extract, at concentration of 100 μg/ml;

The effects of various groups of samples on the telomerase activity of normal human fibroblasts were determined, and the results are shown in Table 3:

TABLE 3

Effects of extracts of the present invention on the telomerase activity of normal human fibroblasts (X ± S, N = 9)

| Group | Extract concentration (μL/mL) | Telomerase activity (ΔA) |
|---|---|---|
| Control group | 0 | 0.303 ± 0.012 |
| Low concentration group | | |
| A1 | 25 | 0.427 ± 0.008* |
| B1 | 25 | 0.389 ± 0.017* |
| C1 | 25 | 0.354 ± 0.012*# |
| Medium concentration group | | |
| A2 | 50 | 0.568 ± 0.015* |
| B2 | 50 | 0.432 ± 0.007*# |
| C2 | 50 | 0.394 ± 0.022*# |
| High concentration group | | |
| A3 | 100 | 0.607 ± 0.009* |
| B3 | 100 | 0.458 ± 0.014*# |
| C3 | 100 | 0.414 ± 0.025*# |

*compared with the control group, P < 0.05;
compared with the solution A of the ginseng-astragalus membranaceus extract, P < 0.05.

Both programmed senescence and exogenous senescence of cells depend on effective regulation between telomerase and telomere. The study found that cells with negative telomerase expression had shortened telomere length and enhanced activity expression of cell senescence related indicators, while cells with positive telomerase expression had elongated telomere length, strong cell division and proliferation ability, and decreased activity expression of cell senescence related indicators. The effective regulation between telomerase and telomere controls occurrence and development of endogenous and exogenous aging. Therefore, it is investigated that the physiological activities of the different extracts affect the telomere length by observing the effects of different extracts on the telomerase activity of normal human fibroblasts.

From the results in Table 3, it can be seen that, for the cells treated with the *ginseng-Astragalus membranaceus* extract, the *Astragalus membranaceus* extract, the *ginseng* extract, and astragaloside in the high, medium and low concentration groups, the telomerase activities were higher than that of control group, which shows that the tested samples can improve the activities of telomerase in the cells, can delay occurrence and development of ageing of the cells. With the concentration increasing, the telomerase activity improved more, and the difference was statistically significant (P<0.05). At the same concentration, the telomerase activity in the group of the *ginseng-Astragalus membranaceus* extract was significantly improved than that of other extract group. The higher the concentration, the greater the difference of the telomerase activity, which can fully demonstrate that the components of the *ginseng-Astragalus membranaceus* extract of the present invention play a synergistic effect, and the effect is significantly better than that of the *ginseng* extract or the *Astragalus membranaceus* extract alone.

Test Example 2

The *ginseng-Astragalus membranaceus* extract prepared in Example 1 of the present invention was formulated and administrated for 9 months (take one tablet daily after meals (each tablet contains 10 mg of the *ginseng-Astragalus membranaceus* extract of the present invention), twice a day). Each participant underwent a comprehensive physical examination and a telomere length test before and after taking the drug (information from all samples was processed blind to prevent the results from being affected by personal information). There are a total of 45 subjects (23 women, 22 men, 25 subjects aged 40~55 years and 20 subjects aged 55~80 years before administration) in the test. The physical examination and the peripheral blood sampling were performed before administration from December 2016 to April 2017 (specific dates are Dec. 16, 2016, Dec. 23, 2016, Dec. 29, 2016, Jan. 3, 2017, Apr. 20, 2017 and Apr. 24, 2017). The physical examination and the peripheral blood sampling were performed after administration from December 2017 to May 2018 (Dec. 8, 2017, Jan. 26, 2018, March 12, 0, 2018, March 30, 0, 2018, April 13, 0, 2018 and May 30, 2018).

Peripheral leukocytes were extracted from the test subjects before and after administration of the *ginseng-Astragalus membranaceus* extract, and the telomere length was detected by LIFELENGTH. The main indicators in the detection were as follows: a 20% of average length of short telomere, a median telomere length, an average telomere length and a corresponding biological age. The detection results were as follows.

The 20% of average lengths of short telomere before and after administration of the *ginseng-Astragalus membranaceus* extract were analyzed. 38 subjects out of the 45 subjects showed varying degrees of increase in the 20% of average length of short telomere, accounting for 84.44%. The average increase was 0.73 Kb, and the increase rate was 15.61%.

The median telomere lengths before and after administration of the *ginseng-Astragalus membranaceus* extract were analyzed. 42 subjects out of the 45 subjects showed varying degrees of increase, accounting for 93.33%. The average increase was 0.86 Kb, and the increase rate was 8.95%.

The average telomere lengths before and after administration of the *ginseng-Astragalus membranaceus* extract were analyzed. 43 subjects out of the 45 subjects showed varying degrees of increase, accounting for 95.56%. The average increase was 0.63 Kb, and the increase rate was 4.51%.

The biological ages before and after administration of the *ginseng-Astragalus membranaceus* extract were analyzed. 41 subjects out of the 45 subjects showed corresponding decrease in the biological age, accounting for 91.11%. The average decrease was 4.34 years. In two of the remaining four subjects, the increase in the biological age was lower than that in actual age.

It can be seen from the results that, the *ginseng-Astragalus membranaceus* extract of the present invention can increase the telomere length of the subject, decrease the biological age of the subject, and effectively fight against aging. Even though the biological age of 2 subjects did not decrease after administration, the increase in their biological age was less than that in the actual age. It can also be said that the *ginseng-Astragalus membranaceus* extract of the present invention has the effect of delaying aging for them.

The medical examination reports before and after administration of the *ginseng-Astragalus membranaceus* extract were analyzed again. According to the main positive results in the medical examination reports of 44 subjects (due to the failure of the peripheral blood leukocyte extract, there is no data in the 45$^{th}$ subject) before and after administrated by the *ginseng-Astragalus membranaceus* extract of the present invention, by comparing and statistically analyzing the main positive results before and after administration, it can be seen that, the extract has effects of decrease in systolic blood pressure of blood vessel (85% of effective rate) and serum triglyceride (73% of effective rate), and no obvious side effects (increased positive results) at present.

Test Example 3

The effects of different *ginseng* processed products, American *ginseng* and commercially available extracts on the telomerase activity were explored.

Main Reagents:

Telomerase activity detection kit (Roche, Switzerland);

CCL137 normal human fibroblast cell line (American Type Culture Collection, ATCC);

*Ginseng* (raw sun-dried)-*Astragalus membranaceus* extract D (an amount of raw medicinal materials, *Astragalus membranaceus*:raw sun-dried *ginseng*=5:1): homemade;

*Ginseng* (red *ginseng*)-*Astragalus membranaceus* extract E (an amount of raw medicinal materials, *Astragalus membranaceus*:red *ginseng*=5:1): homemade;

*Ginseng* (active *ginseng*)-*Astragalus membranaceus* extract F (an amount of raw medicinal materials, *Astragalus membranaceus*:active *ginseng*=5:1): homemade;

American *ginseng-Astragalus membranaceus* extract G (an amount of raw medicinal materials, *Astragalus membranaceus*: American *ginseng*=5:1): homemade;

Extract H: commercially available *Astragalus membranaceus* extract (extraction ratio of 25:1, Chengdu Jintaihe Biotechnology Co., Ltd.): commercially available *ginseng* extract (extraction ratio of 25:1, Shandong Tangzheng Biotechnology Co., Ltd.)=8:1;

Extract J: commercially available *Astragalus membranaceus* extract (extraction ratio of 20:1, Xi'an Qingzhi Biotechnology Co., Ltd.): commercially available *ginseng* extract (extraction ratio of 25:1, Jilin Ruilong Pharmaceutical Co., Ltd.)=8:1;

Extract K: 24.00% of Astragaloside (specification:98%), 2.50% of ginsenoside Rg1 (specification:98%), 4.00% of ginsenoside Re (specification:98%) and 0.25% of ginsenoside Rb1 (specification:98%), the remaining ingredients of corn dextrin;

Astragaloside (specification: 98%), L: purchased from Chengdu Jintaihe Biotechnology Co., Ltd.;

Ginsenoside Rg1 (specification:98%), ginsenoside Re (specification 98%) and ginsenoside Rb1 (specification:98%), purchased from Shanghai Yuanye Biotechnology Co., Ltd.

The homemade extracts were prepared by the following methods:

10 g of medicinal powders were weighed, and added with 100 mL of water to soak for 3 hours, then heated to perform reflux extraction for 2 hours, and filtered. The filter residue was then reflux-extracted with 80 mL of water for 2 hours, and filtered, and the filtrate was pooled. The pooled filtrate was passed through macroporous adsorption resin D101 and then washed with water, 20% ethanol, and 70% ethanol respectively. The 70% ethanol eluant was collected, added with 0.5% (by mass of the medicinal powder) of the complex enzyme (β-glucosidase and xylanase at the weight ratio of 3:1) after removing the ethanol, adjusted to pH of 5 to 6, stirred at 40 to 55° C. for 5 hours, and filtered. The filtrate was membrane-filtered with a ceramic nanofiltration membrane (molecular weight cut-off of 200-1000 Da), concentrated, and spray-dried to obtain the corresponding extract.

The contents of various components in extracts D-F, H and J were detected by a liquid chromatography. The contents of astragaloside, ginsenoside Rg1, ginsenoside Re and ginsenoside Rb1 were shown as follow.

TABLE 4

|  | Extract D | Extract E | Extract F | Extract H | Extract J |
|---|---|---|---|---|---|
| Astragaloside (%) | 25.372 | 24.965 | 26.598 | 1.236 | 1.069 |
| Ginsenoside Rg1 (%) | 2.328 | 2.268 | 3.012 | 0.365 | 0.289 |
| Ginsenoside Re (%) | 3.891 | 3.681 | 3.692 | 0.489 | 0.426 |
| Ginsenoside Rb1 (%) | 0.257 | 0.289 | 0.286 | 0.127 | 0.096 |

The test methods and procedures for detection of the telomerase activity were the same as the Test Example 1, and the measured results were shown in Table 5.

TABLE 5

Effects of the different extracts on the telomerase activity of normal fibroblasts (X ± S, N = 9)

| Groups | Extract concentration (ug/mL) | Telomerase activity (ΔA) |
|---|---|---|
| Control group | 0 | 0.298 ± 0.008* |
| Medium concentration group | | |
| D1 | 50 | 0.585 ± 0.009* |
| E1 | 50 | 0.568 ± 0.011* |
| F1 | 50 | 0.579 ± 0.016* |
| G1 | 50 | 0.412 ± 0.009 |
| H1 | 50 | 0.321 ± 0.009* |
| J1 | 50 | 0.314 ± 0.012*# |
| K1 | 50 | 0.446 ± 0.018*# |
| L1 | 50 | 0.453 ± 0.014*# |
| High concentration group | | |
| D2 | 100 | 0.628 ± 0.009* |
| E2 | 100 | 0.632 ± 0.017* |
| F2 | 100 | 0.618 ± 0.011* |
| G2 | 100 | 0.438 ± 0.014*# |
| H2 | 100 | 0.329 ± 0.010*# |
| J2 | 100 | 0.336 ± 0.008*# |
| K2 | 100 | 0.533 ± 0.006*# |
| L2 | 100 | 0.436 ± 0.011* |

*compared with the control group, P < 0.05;
compared with the raw sun-dried ginseng-astragalus membranaceus extract, P < 0.05.

According to the results in Table 5, the extracts D, E and F obtained by extracting from the different combinations of *Astragalus membranaceus* with *ginseng* processed products, raw sun-dried *ginseng*, red *ginseng*, and active *ginseng* significantly improved the telomerase activity of normal human fibroblasts, and had the similar effects to that of the extract of *ginseng* and *Astragalus membranaceus*.

The extract obtained by extracting from the combination of *Astragalus membranaceus* and American *ginseng* (replacing for *ginseng*) can improve the telomerase activity of human fibroblasts, but had the relatively poor effect than the *ginseng-Astragalus membranaceus* extract.

The extract obtained by mixing the commercial available *Astragalus membranaceus* extract and the commercial available *ginseng* extract only slightly improved the telomerase activity of human fibroblasts, and had weak anti-aging activity.

The extract K obtained by mixing the finished astragaloside, ginsenoside Rg1, ginsenoside Re and ginsenoside Rb1 at the content range determined for the extract of the present invention can improve the telomerase activity of normal human fibroblasts to a certain extent. The extract K at high concentration was significantly superior to astragaloside and had a better effect.

The foregoing examples are only embodiments of the present invention and do not limit the protection scope of the present invention. Any modification of equivalent structure or equivalent process made by using the disclosure of the description of the present invention, or direct or indirect application to other related technical fields, is also included in the protection scope of the present invention.

What is claimed is:

1. A mixture of extracts, wherein its raw material comprises, by a weight of the raw material, 1 part of *ginseng* and/or American *ginseng*, 4 to 8 parts of *Astragalus membranaceus*; wherein
   the mixture of extracts comprises 20 to 30% of astragaloside, 1 to 5% of ginsenoside Rg1, 2 to 6% of ginsenoside Re, and 0.1 to 0.5% of ginsenoside Rb1; and
   a content of total saponins in the mixture of extracts is from 75 to 95% and a content of total polysaccharide is from 3 to 10%.

2. The mixture of extracts according to claim 1, wherein there are at least 6 characteristic peaks in high-performance liquid chromatography fingerprints of the mixture of extracts, and wherein taking the characteristic peak of ginsenoside Re as a reference peak, relative retention times for the 6 characteristic peaks with respect to the reference peak are 0.95, 1.00, 1.80, 2.13, 2.36, and 3.20 respectively.

3. The mixture of extracts according to claim 2, wherein relative peak areas of characteristic peaks with relative retention times of 0.95, 1.00, 1.80, 2.13, 2.36 and 3.20 are 48.41%, 100.00%, 107.04%, 48.70%, 340.51% and 54.83%, respectively.

4. The mixture of extracts according to claim 2, wherein a detection method of high-performance liquid chromatography (HPLC) fingerprints is used for a qualitative and/or quantitative detection by HPLC, wherein HPLC conditions comprise:
   column: C18 silica gel column;
   mobile phase: water and acetonitrile, and
   a gradient elution procedure:

| Time (min) | Water (V %) | Acetonitrile (V %) |
|---|---|---|
| 0 | 80~90 | 10~20 |
| 30~35 | 60~70 | 30~40 |
| 70~85 | 10~30 | 70~90. |

5. The mixture of extracts according to claim 4, wherein the HPLC conditions further comprise:
   ① column size: 150*3.9 mm, 5 μm;
   ② Column temperature: 25~35° C.; preferably 30° C.;
   ③ flow rate: 0.8~1.2 mL/min; preferably 1.00 mL/min;
   ④ detection wavelength: 200~205 nm, preferably 203 nm.

6. The mixture of extracts according to claim 1, wherein its raw material comprises, by a weight of the raw material, 1 part of *ginseng* and/or American *ginseng*, 4 to 6 parts of *Astragalus membranaceus*, wherein
   the mixture of extracts comprises 22 to 28% of astragaloside, 1.8 to 4% of ginsenoside Rg1, 3 to 5% of ginsenoside Re, and 0.2 to 0.3% of ginsenoside Rb1; and the content of total saponins is 80 to 90%, and the content of total polysaccharides is 5 to 8%.

7. The mixture of extracts according to claim 2, wherein the high-performance liquid chromatography fingerprints of the mixture of extracts further comprise 11 characteristic peaks, wherein relative retention times for the 11 characteristic peaks with respect to the reference peak are 1.66, 1.69, 1.73, 1.86, 1.88, 1.94, 1.99, 2.02, 2.28, 2.40, and 2.45 respectively.

8. The mixture of extracts according to claim 2, wherein relative peak areas of characteristic peaks with relative retention times of 1.66, 1.69, 1.73, 1.86, 1.88, 1.94, 1.99, 2.02, 2.28, 2.40 and 2.45 are 9.52%, 17.21%, 2.61%, 4.16%, 22.88%, 10.92%, 16.34%, 8.33%, 3.37%, 5.14% and 14.59%, respectively.

9. The mixture of extracts according to claim 4, wherein the elution procedure is as follows:

| Time (min) | Water (V %) | Acetonitrile (V %) |
|---|---|---|
| 0 | 85 | 16 |
| 33 | 66 | 34 |
| 78.5 | 20 | 80. |

10. A preparation method of the mixture of extracts according to claim 2, wherein the method comprises:
  (1) performing extraction from the raw material with water;
  (2) performing enrichment with macroporous adsorption resin;
  (3) performing enzymolysis;
  (4) performing membrane filtration, wherein molecular weight cut-of is 200~1000 Da; and
  (5) performing solid-liquid separation.

11. The preparation method according to claim 10, wherein in the step of extraction with water, a liquid/material ratio of water to the raw material is 5-15:1 mL/g; and the extraction with water is repeated 1 to 4 times.

12. The preparation method according to claim 10, wherein the enrichment with macroporous adsorption resin is to obtain a part by passing an extraction liquid extracted with water through non-polar or weak polar macroporous adsorption resin to performing adsorption, washing with water, 10~40% ethanol, and 60~80% ethanol successively, and collecting a 60~80% ethanol eluent.

13. The preparation method according to claim 10, wherein the enzymolysis is enzymolysis of the material obtained after the enrichment with macroporous adsorption resin, wherein the enzyme is a complex enzyme composed of β-glucosidase and Xylanase at a weight ratio of 2-4:1; and
  the enzymolysis conditions are performing enzymolysis with the complex enzyme of 0.2 to 1.0% by a weight of the raw material at pH of 5~6 at 40 to 55° C.

14. The preparation method according to claim 12, wherein washing is performed with water, 25~30% ethanol, and 70~80% ethanol successively, and a 70~80% ethanol eluent is collected.

* * * * *